United States Patent [19]
Kensey

[11] Patent Number: 5,250,024
[45] Date of Patent: Oct. 5, 1993

[54] SYSTEM FOR INTRODUCING A THERAPEUTIC AGENT INTO THE RECTUM

[75] Inventor: Kenneth Kensey, Chester Springs, Pa.

[73] Assignee: Kensey Nash Corporation, Exton, Pa.

[21] Appl. No.: 934,378

[22] Filed: Aug. 24, 1992

[51] Int. Cl.⁵ ............................................. A61M 31/00
[52] U.S. Cl. .................................. 604/275; 604/257; 604/276
[58] Field of Search .............................. 604/257-262, 604/275, 276, 279, 48

[56] References Cited

U.S. PATENT DOCUMENTS

| | | | |
|---|---|---|---|
| 330,084 | 11/1885 | Allen | 604/275 |
| 337,249 | 3/1886 | Conkle | 604/275 |
| 343,252 | 6/1886 | Philbrick | 604/276 |
| 559,417 | 5/1896 | Spencer | 604/276 |
| 906,711 | 12/1908 | Hill et al. | 604/276 |
| 925,718 | 6/1909 | Pearl | 604/275 |
| 1,555,656 | 9/1925 | Gilmartin | 604/276 |
| 1,602,750 | 10/1926 | Cole | 604/275 |
| 1,692,922 | 11/1928 | Berg | 604/276 |
| 2,007,069 | 7/1935 | Berg | 604/276 |
| 2,267,909 | 12/1941 | Grauert | 604/276 |
| 2,438,073 | 3/1948 | Saur | 604/277 |
| 2,583,298 | 1/1952 | Kowan | 604/276 |
| 4,596,554 | 6/1986 | Dastgeer | 604/276 |
| 4,986,822 | 1/1991 | Anderson | 604/276 |

*Primary Examiner*—Ralph Lewis
*Attorney, Agent, or Firm*—Caesar, Rivise, Bernstein, Cohen & Pokotilow

[57] ABSTRACT

A device for administering a liquid into the bowel of a person. The device comprises a rigid conduit, a manually actuatable pump, and a reservoir holding the liquid. The conduit is of a general J-shape having an elongated straight proximal section and a curved distal section terminating in a tip having an aperture therein. The elongated proximal section is sufficiently long that when the person is seated on a toilet with the proximal section located between the person's legs the tip is located at the person's anus, so that he/she can readily insert the tip into the anus by manually manipulating the proximal section of the conduit. The pump is coupled to the proximal section of the conduit and is arranged to be squeezed by the person to pump the liquid from the reservoir through the conduit and out the aperture into the person's bowel.

8 Claims, 1 Drawing Sheet

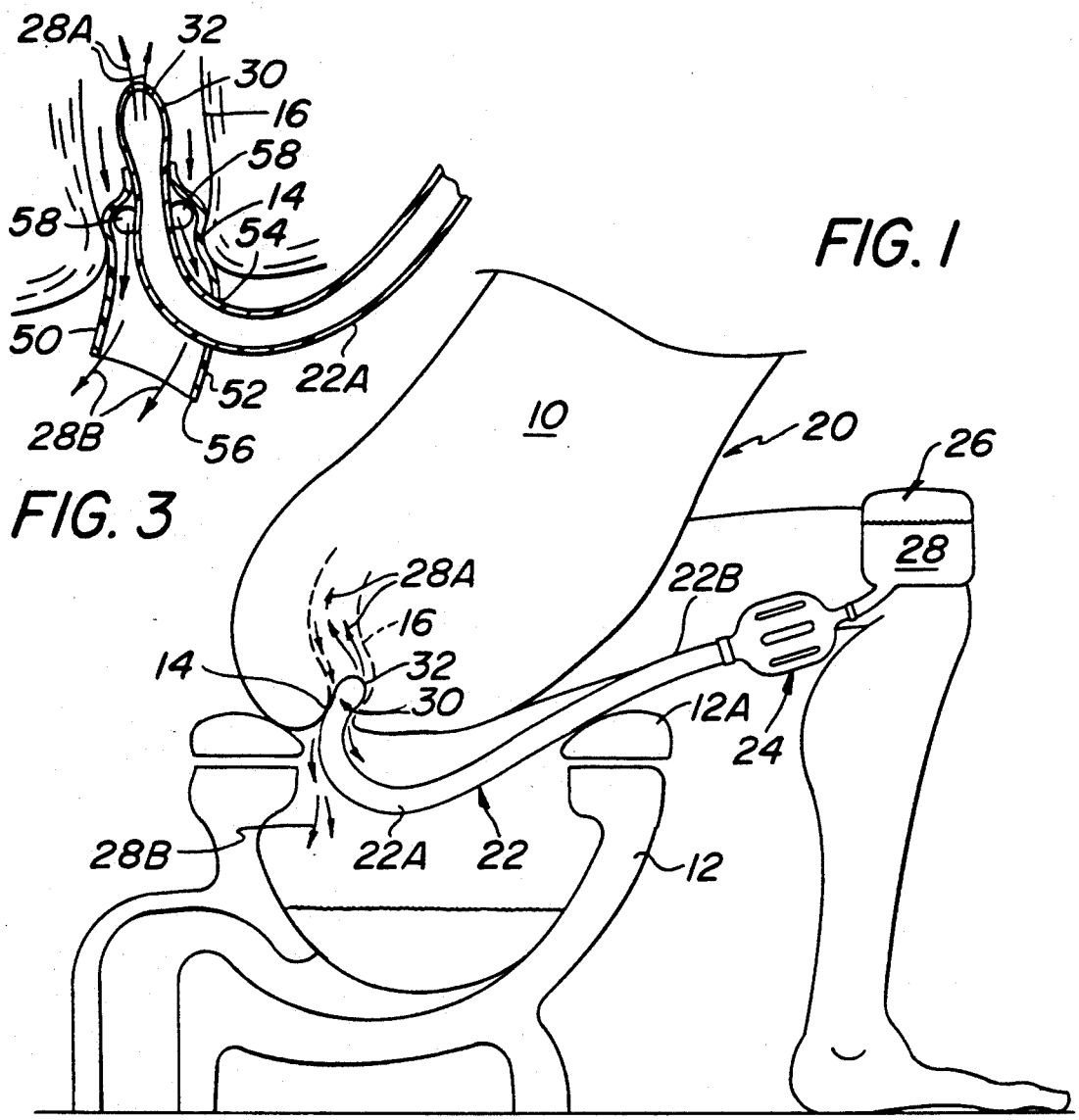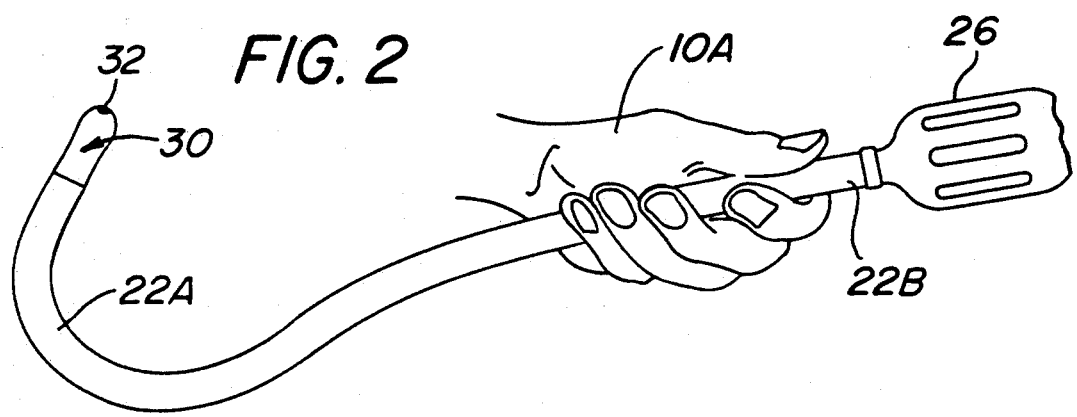

5,250,024

SYSTEM FOR INTRODUCING A THERAPEUTIC AGENT INTO THE RECTUM

BACKGROUND OF THE INVENTION

This invention relates generally to medical devices and more particularly to devices which are suitable for use by a lay person to readily self-administer any type of therapeutic agent into his/her bowel through the rectum.

One common problem with aged or infirm persons is the tendency to have fecal impactions, thereby necessitating an enema or some other similar procedure for relief. Prior art devices for providing an enema or otherwise irrigating the person's bowel leave much to be desired from the standpoint of ease of use. In this regard prior art devices tend to be generally somewhat difficult to insert through the anus by the aged or infirm.

OBJECTS OF THE INVENTION

Accordingly, it is a general object of this invention to provide a device which overcomes the disadvantages of the prior art and which fulfill the need set forth above.

It is another object of this invention to provide a device for enabling a persons to self-administer a liquid rectally while seated on a toilet.

It is still another object of this invention to provide a device which is simple in construction and easy to use to enable a person to self-administer a liquid through his/her rectum into the bowel.

SUMMARY OF THE INVENTION

These and other objects of this invention are achieved by providing a device for administering a liquid into the bowel of a person through the person's anus. The device comprises an introducer means and manually actuatable pump means. The introducer means comprising a relatively rigid hollow conduit having a curved distal section and an elongated proximal section, with the curved distal section terminating at a free end in the form of a tip configured for ready passage into the anus.

The elongated section of the conduit has a proximal end and is sufficiently long that when the person is seated on a toilet with the proximal end located between the person's legs adjacent the person's thighs the tip is located at the person's anus, whereupon the person can readily insert the tip into the anus by manually manipulating the proximal section of the conduit.

The free end of the conduit has at least one aperture therein. The pump means is coupled to the proximal section of the conduit and is arranged to be operated by the person to pump the liquid through the conduit and out the apertures in the distal end into the person's bowel.

BRIEF DESCRIPTION OF THE DRAWING

Other objects and many of the attendant advantages of this invention will be readily appreciated as the same becomes better understood by reference to the following detailed description when considered in connection with the accompanying drawings wherein:

FIG. 1 is a side elevational view, partially in section, showing the device of the subject invention in one typical use by a person seated on a toilet to effect irrigation and flushing of the bowel;

FIG. 2 is an enlarged side elevational view of a portion of the device of FIG. 1 s showing how it is grasped by the user to operate it; and FIG. 3 is an enlarged side elevational view, partially in section, showing an alternative embodiment of the tip portion of the device particularly suited for effecting continuous heavy irrigation and flushing of the bowel.

DETAILED DESCRIPTION OF THE PREFERRED EMBODIMENT

Referring now in greater detail to the figures there is shown at 20 in FIG. 1 one embodiment of a device constructed in accordance with this invention. The device 20 is arranged to enable a person to self-administer an irrigation and/or therapeutic liquid into his/her rectum for any desired purpose. For example, one such use of the device 20 is to irrigate and flush the bowel of fecal impactions. Other types of procedures can also be accomplished. To that end any type of liquid irrigation and/or therapeutic agent, such as soap water, salt water, oils (mineral or vegetable), may be used by the device 20. Moreover, the device 20 may be used to deliver a suppository into the user's rectum.

In FIG. 1 the device 20 is shown in one typical use for irrigating and flushing the bowel of a person. As can be seen therein the device 20 basically comprises a generally J-shaped tube 22 or conduit, an associated pump 24, and an associated reservoir chamber 26. The reservoir chamber serves to hold the irrigation and/or therapeutic liquid 28 therein until it is ready to be introduced into the user's rectum.

The tube 22 is formed of a substantially rigid material, e.g., polyethylene, polypropylene, etc., and includes a curved distal section 22A and a generally linear, elongated proximal section 22B. The curved distal section 22A terminates in a tip 30 having an outlet aperture 32 at its free end. The pump 24 is hand actuatable, as will be described later, and is secured to the proximal end of the J-tube section 22B to pump the liquid 28 into the J-tube 22 and out the outlet aperture 32. The liquid 28 is provided to the pump 24 from the reservoir 26. The reservoir 26 comprises a hollow chamber which is connected to the opposite side of the pump 24 as the J-tube 22.

The device 20 is arranged so that it can be readily used by any person, even if aged or infirm, to self-administer the liquid into the person's bowel. To accomplish that task in the most expeditious manner the device 20 is preferably used while the person 10 is seated on a toilet 12 like shown in FIG. 1. However, if the person is unable to be seated on a toilet the device 20 can be used by the person (or by an aide if the person is too infirm to use the device by himself/herself) so long as the person is in some supported position wherein his/her legs are slightly apart and his/her anus unobstructed.

In accordance with one aspect of this invention the elongated proximal section 22B of the J-tube 22 is of a sufficient length so that when the device is in the orientation shown in FIG. 1 the proximal end of the J-tube or the pump 24 will be located between the user's legs while the tip 30 of the device will be located adjacent the user's anus. In this position the user can readily grasp either the proximal end of the J-tube section 22B in one hand 10A (as shown in FIG. 2) while the other hand (not shown) holds the pump 24 so that he/she can manipulate the device 20 until the tip 30 enters his/her anus 14 passes beyond the anal sphincter and extends into the bowel 16. An intermediate portion of the J-tube section 22B may be rested or supported upon the toilet seat 12A during the insertion procedure to act as a fulcrum for facilitating the insertion of the tip 30 into the anus. This modality of use can be of particular utility if the person is aged, infirm, weak or unsteady. It is also contemplated that one or more handles or projections may, if desired, be provided on the device 20 to aid the person to manipulate the device into his/her anus.

In accordance with a preferred embodiment of this device the tip 30 of J-tube 22 is constructed so that it is atraumatic and will freely enter the anus and pass therethrough into the bowel with very little resistance. Thus, the tip is formed of an atraumatic material, e.g., a firm silicone elastomer. The tip may be of any suitable shape adapted for easily entrance into the anus. One particularly effective shape is that of the COMFORTIP(TM) tip used on the disposable squeeze bottle of the enema product sold by C.B. Fleet Company, Inc., of Lynchburg Va. under the registered trademark FLEET.

The pump 24 may be of any suitable construction arranged for easy operation by the user of the device to pump the liquid through the J-tube into the user's bowel once the device 20 is in place like that shown in FIG. 1. One preferable construction for the pump is that shown in FIGS. 1 and 2. As can be seen therein the pump 24 consists of a hollow bladder formed of a resilient material, e.g., rubber. The pump is arranged to be readily squeezed in the user's hand (or hands, if necessary) to draw a vacuum in the reservoir chamber. This action carries the irrigation/therapeutic liquid from that chamber to the interior of the pump from whence it is forced through the J-tube 22 and out the outlet into the person's bowel. The path of liquid flow into the bowel is shown by the arrows designated by the reference numeral 28A in FIG. 1. The irrigation and/or therapeutic agent, along with bowel resident material, e.g., fecal matter, may then flow about the exterior of the tip 24 and out of the anus as shown by the arrows designated by the reference numeral 28B.

It should be pointed out at this juncture that the hand squeezable pump 24 is merely one of many types of pumps which can be used. Thus, other types of actuatable pumps may be used in lieu of a manually sqeezable pump. For example, the pump may be powered from a self-contained power source, e.g., a battery, or may be powered from an external power source, e.g., household current.

In FIG. 3 there is shown the distal end of an alternative embodiment of a device constructed in accordance with this invention. This embodiment of the device 20 is arranged to facilitate the continuous heavy irrigation and drainage of impacted fecal material from the bowel upon introduction of the liquid 28 therein. Thus, the distal end of the alternative embodiment of the device of this invention includes a drainage shroud 50 disposed over the free end of the device's tip 30. In all other respects the alternative embodiment of the device is identical to that described heretofore. The shroud basically comprises a hollow member having a sidewall 52 the distal end of which is secured to the tip 30 contiguous with and surrounding the aperture. 32. The sidewall 52 of the shroud covers the portion of the curved distal section 22A of the device 20 contiguous with the tip 30, with a portion of that section extending through a hole 54 in an intermediate portion of the shroud's sidewall. The proximal end of the sidewall of the shroud terminates is in the form of an outlet tube 56. A plurality of apertures 58 are located in the shroud's sidewall 54 and extending equidistantly about its periphery adjacent the point at which the shroud merges with the tip 30.

The length of the shroud 50 is selected so that when the tip 30 of the device 20 is in place within the person's bowel, the outlet tube 54 is located outside the person's anus as shown in FIG. 3. With the device 20 in place as just described an irrigation and/or therapeutic liquid 28 can be introduced into the bowel in the same manner as described earlier so that the liquid enters the bowel in the direction of the arrows 28A. Material within the bowel, e.g., fecal matter, which has been soften or otherwise freed by the introduced liquid 28 may then pass with the liquid through the apertures 58 into the interior of the shroud for ready passage through the outlet tube 56 into the toilet as shown by the arrows 28B.

As will be appreciated from the foregoing the device 20 is simple in construction and can be made at a relatively low cost. This renders the device suitable for one time use, e.g., it may be disposable. It can also be reused since it can be readily cleaned and/or disinfected. To that end it may be cleaned/disinfected after use by introducing any liquid cleaning and/or disinfecting agent into the reservoir chamber and then operating the pump to force that agent through the device and out its aperture. The exterior of the device can be cleaned and/or disinfected by immersing the device in the liquid cleaning and/or disinfecting agent. To facilitate the cleaning and/or disinfecting of the device 20 it may be constructed so that its various components can be disassembled from each other.

The use of a separate reservoir chamber 26 for holding the irrigation and/or therapeutic liquid agent is optional. Thus, the separate reservoir chamber may be eliminated and the irrigation and/or therapeutic liquid may be held within the hollow interior of the bladder pump itself. If a separate reservoir chamber is used it may include a removable cover or lid (not shown) to enable the it to be filled with an liquid desired by the user.

As should be appreciated from the foregoing the device of this invention allows the self administration of a liquid agent into the rectum while the person is preferably seated on a toilet. For aged or infirm persons, or others with limited flexibility, the device allows access to the rectum without contortion and ensures drainage of fecal impactions without embarrassment. While the device of this invention is arranged to enable the self-administration of the irrigation/therapeutic liquid, it is of course apparent that it may be used on a person by an aide if the person is incapable or does not desire to use the device on himself/herself.

Without further elaboration the foregoing will so fully illustrate my invention that others may, by applying current or future knowledge, adopt the same for use under various conditions of service.

I claim:

1. An integrated device for administering a liquid into the bowel of a person through the person's anus, said device comprising introducer means, reservoir means, and manually actuatable pump means coupled to said reservoir means, said reservoir means holding said liquid therein, said introducer means comprising a relatively rigid generally J-shaped hollow conduit having a curved distal end section and an elongated generally linear proximal section, said curved distal end section terminating at a free end portion in the form of a tip configured for ready passage into said anus, said elongated generally linear proximal section having a proximal end and being sufficiently long that when said person is in a seated orientation said proximal end may be located between said person's legs adjacent the thighs with said tip being located adjacent said anus, whereupon said person can readily insert said tip into said anus by manually manipulating said proximal section, said free end portion having at least one aperture therein, said pump means and said reservoir means being mounted on and supported by said proximal section, said pump means being arranged to be operated by said person to pump said liquid from said reservoir means through said conduit and out said aperture into the bowel of said person.

2. The device of claim 1 wherein said pump means comprises a manually actuatable member.

3. The device of claim 2 wherein said manually actuatable member comprises a sqeezable hollow bladder.

4. The device of claim 3 additionally comprising a reservoir chamber coupled to said pump means for holding said liquid therein.

5. The device of claim 2 additionally comprising a reservoir chamber coupled to said pump means for holding said liquid therein.

6. A device for administering a liquid into the bowel of a person through the person's anus, said device comprising introducer means, manually actuatable pump means, and a shroud, said manually actuatable pump means being coupled to said introducer means, said introducer means comprising a relatively rigid hollow conduit having a curved distal end section and an elongated proximal section, said curved distal end section terminating at a free end portion in the form of a tip configured for ready passage into said anus, said elongated section of said conduit having a proximal end and being sufficiently long that when said person is in a seated orientation said proximal end may be located between said person's legs adjacent the thighs with said tip being located adjacent said anus, whereupon said person can readily insert said tip into said anus by manually manipulating said proximal section, said free end portion having at least one aperture therein, said pump means being coupled to said proximal section and being arranged to be operated by said person to pump said liquid through said conduit and out said aperture into the bowel of said person, said shroud comprising a hollow member having a distal end located over said tip for engagement with the person's anus, and a proximal end in the form of an open ended tube, whose open end is arranged to extend out of said anus when said tip is in place within said bowel, said shroud including at least one aperture therein through which material located within said bowel may pass after said liquid is introduced into said bowel, whereupon said material can pass out through said open ended tube for collection or disposal.

7. The device of claim 6 wherein said pump means comprises a manually actuatable member.

8. The device of claim 7 wherein said manually actuatable member comprises a sqeezable hollow bladder.

* * * * *